United States Patent [19]

Turner et al.

[11] Patent Number: 4,532,334
[45] Date of Patent: Jul. 30, 1985

[54] PROCESS FOR MAKING GIBBERELLINS

[76] Inventors: John V. Turner, P.O. Box 4, Canberra, ACT, Australia, 2600; Russell A. Bell, 84 Hopkins Ct., Dundas, Canada, L9H 5M8

[21] Appl. No.: 437,281

[22] Filed: Oct. 28, 1982

[30] Foreign Application Priority Data

Oct. 30, 1981 [AU] Australia .................. PF1367

[51] Int. Cl.³ ............................. C07D 307/94
[52] U.S. Cl. ................................. 549/297
[58] Field of Search .......................... 549/297

[56] References Cited

U.S. PATENT DOCUMENTS 4,241,221 12/1980 Grudzinskas et al. ............. 560/21

OTHER PUBLICATIONS

Murofushi et al., Chem. Abs. 88: 7093h.

*Primary Examiner*—Jane T. Fan
*Attorney, Agent, or Firm*—Bacon & Thomas

[57] ABSTRACT

Processes for the preparation of 1,2-dihydro-3-hydroxy gibberellin acids of general formula (1) from precursor gibberellin acids that employs conditions which (a) do not require prior protection of the free carboxylic acid group; (b) preserve the Δ(16)-olefinic bond and the lactone; and (c) enable the stereochemistry of the hydroxyl moiety at position 3 to be controlled, enabling access to the individual stereoisomers of the 1,2-dihydro-3-hydroxy gibberellin acids; said processes comprising the reaction of either a 3-keto gibberellin of general formula (2), or of the general formula (3), or a mixture thereof, in the presence or absence of a proton source depending on the particular precursor gibberellin acid, with a compound of general formula (4):

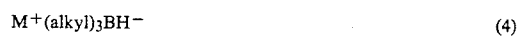

$M^+(alkyl)_3BH^-$ (4)

wherein $M^{30}$ represents a monovalent cation.

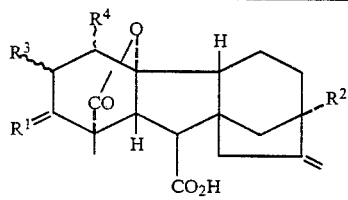

|     | $R^1$ | $R^2$ | $R^3$ | $R^4$ |
|-----|-------|-------|-------|-------|
| (1) | OH, H | H, OH, alkoxy, substituted alkoxy, acyloxy | H | H |
| (2) | O | as above | together, a valence bond | |
| (3) | O | as above | H | H |

27 Claims, No Drawings

PROCESS FOR MAKING GIBBERELLINS

This invention relates to a process for the preparation of compounds of the gibberellin group, including both naturally occurring members and various modified analogues.

Gibberellins are a well-known group of phytohormones which occur naturally in all higher plants in minute quantities. They have profound and diverse effects on plant development and are consequently important compounds in agriculture and horticulture. For example, it has been shown that certain gibberellins can double the yield of barley and wheat from a given acreage, crop failure due to frost or poor pollination can be reversed, dormancy can be broken, and that senescence and fruit-fall can be delayed.

Gibberellins are based on the tetracyclic ring structure of formula (1) which illustrates the ring numbering but not the precise stereochemistry. Individual gibberellins are given the designation $GA_n$, where n(integer) is derived from the chronological order of discovery.

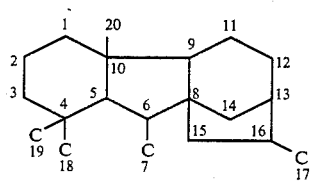
(1)

A factor limiting the routine and widespread commercial use of gibberellins has been that $GA_3(2)$ and mixtures of $GA_4(3)$ and $GA_7(4)$ are the only C19-gibberellins which can be produced in quantity by fermentation. The preparation of other gibberellins in significant quantities can only be achieved by laboratory chemical processes.

In these laboratory processes, an important step is the conversion of $\Delta(1)$-gibberellins of general formula (5) and their derivatives into the corresponding 1,2-dihydroanalogues of general formula (6).

Two reports of the selective hydrogenation of the $\Delta(1)$ bond have been published in the chemical literature [B E Cross, R H B Galt and J R Hanson, *Tetrahedron*, 18, 451 (1962); D F Jones and P McCloskey, *J. Appl. Chem.*, 13, 324 (1963)]. However, these approaches often lead to the hydrogenolysis of the allylic lactone and hydrogenation of the $\Delta(16)$-bond.

These problems have been solved by more recent procedures based upon conjugate hydride-reduction of the readily available $\Delta(1)$-3-one methyl esters of general formula (7). [I A Gurvich, N S Kobrina and V F Kucherov, *Bull. Acad. Sci. U.S.S.R.*, 1668 (1969); M H Beale and J MacMillan, *J.C.S. Perkin 1*, 877 (1980); B Voigt, G Adams, N S Kobrina, E P Serebryakov and N D Zelinsky, *Z. Chem.*, 17, 373 (1977); Z J Duri, B M Fraga and J R Hanson, *J.C.S. Perkin 1*, 161 (1981); L Lombardo, L N Mander and J V Turner, *Aust. J. Chem.*, 34, 745 (1981)]. However, esters of general formula (8) with the unnatural 3α-(equatorial)-hydroxy group, rather than the esters of the general formula (9) with the naturally occurring 3β-(axial)-hydroxy group, are mainly obtained as a consequence of the final hydride-delivery to C(3) along the less hindered β-vector.

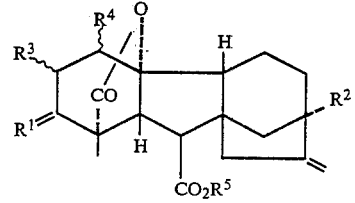

| | $R^1$ | $R^2$ | $R^3$ | $R^4$ | $R^5$ |
|---|---|---|---|---|---|
| (2) | βOH, αH | OH | | together, a valence bond | H |
| (3) | βOH, αH | H | H | H | H |
| (4) | βOH, αH | H | | together, a valence bond | H |
| (5) | OH, H | OH or H | | together, a valence bond | H |
| (6) | OH, H | OH or H | H | H | H |
| (7) | O | OH or H | | together, a valence bond | $CH_3$ |
| (8) | αOH, βH | OH or H | H | H | $CH_3$ |
| (9) | βOH, αH | OH or H | H | H | $CH_3$ |

A second disadvantage of the above conjugate hydride-reduction procedures is that only the free C(6)-carboxylic acids, and not the corresponding esters, are produced by fermentation. Consequently, the above hydride-reduction processes to produce 3-hydroxy-6-carboxylic gibberellins necessitate at least two additional steps in the reaction sequence—the preparation of an ester from the acid and then the hydrolysis back to the free acid after the hydride reduction. Further, protection of the C(3)-hydroxy group is desirable to prevent retro-aldol processes during the hydrolysis. Also, the hydrolysis of the ester often leads to the concurrent hydrolysis of the lactone.

It is an object of the present invention to provide a process for the preparation of 1,2-dihydro-3-hydroxy gibberellin acids from precursor gibberellin acids, that employs conditions which (a) do not require prior protection of the free carboxylic acid group; (b) preserve the $\Delta(16)$-olefinic bond and the lactone; and (c) enable the stereochemistry of the hydroxyl moiety at position 3 to be controlled, enabling access to the individual stereoisomers of the 1,2-dihydro-3-hydroxy gibberellin acids.

It will be appreciated that the various compounds referred to throughout this specification are chiral and the present invention relates both to the individual stereoisomers and to any mixtures thereof whether these mixtures include enantiomers and/or diastereoisomers. In accordance with accepted nomenclature, the dotted lines used in the formulae throughout this specification indicate that the attached group lies behind the general plane of the ring system, i.e., that the group is in an α-configuration; whilst thickened lines indicate that the attached group lies in front of the general plane of the system, i.e., that the group is in a β-configuration. The wavy lines used in the formulae throughout this specification indicate that the attached group is present in an α- or β-configuration or is present in both α- and β-configurations, thus including not only all the individual stereoisomers thereof, but also all mixtures of such stereoisomers, including optically inactive racemic mixtures of enantiomers and optically active mixtures in which one enantiomer is present in excess relative to the other enantiomer, as well as mixtures of diastereoisomers.

According to one aspect of the present invention, there is provided a process for the preparation of compounds of the general formula (10):

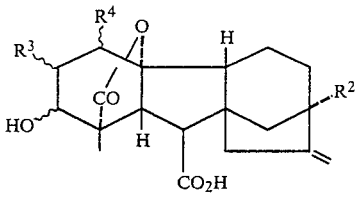
(10)

wherein
$R^2$ is a radical selected from the group consisting of H, OH, alkoxy, substituted alkoxy and acyloxy;
$R^3$ and $R^4$ are radicals separately selected from the group consisting of H and alkyl;
comprising the reaction of a $\Delta(1)$-3-keto gibberellin of the general formula (11):

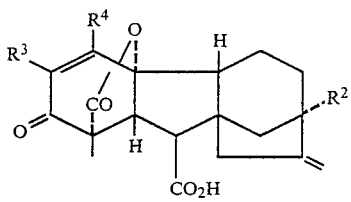
(11)

wherein the radicals $R^2$, $R^3$ and $R^4$ are as hereinbefore defined,
in the presence of a proton source, with a compound of the general formula (12):

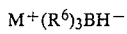
$M^+(R^6)_3BH^-$ (12)

wherein $M^+$ represents a monovalent cation and $R^6$ represents an alkyl group.

As used throughout the specification, the terms "alkoxy", "substituted alkoxy", "acyloxy" and "alkyl" are used to denote the following:
"alkoxy"—radicals in which the alkyl portion is a straight- or branched-chain hydrocarbon of 1 to 10 carbon atoms;
"substituted alkoxy"—alkoxy radicals which may optionally be substituted by one or more radicals separately selected from the group consisting of alkyl, alkenyl, alkynyl, alkoxy or halogen;
"acyloxy"—radicals derived from carboxylic or sulphonic acids, which may optionally be substituted by one or more radicals separately selected from the group consisting of alkyl, alkenyl, alkynyl, alkoxy or halogen.
"alkyl"—straight- or branched-chain hydrocarbon of 1 to 10 carbon atoms.

A proton source is needed which decomposes in situ the intermediate enol borate from an initial 1,4-addition of hydride, to unmask the C(3)-ketone for the final 1,2-reduction. Several proton sources can be used, including alkanols and hydrogenophosphate salts. Preferably, the proton source is selected from ethanol, isopropanol, potassium or sodium dihydrogenphosphate, or dipotassium hydrogenophosphate. More preferably, potassium dihydrogenphosphate is used, as this proton source serves to buffer the reaction mixture without rapidly destroying the trialkylborohydrides.

The trialkylborohydrides of general formula (12) are suitable for the 1,2-hydride reduction of 1,2-dihydro-3-keto gibberellins to their corresponding 1,2-dihydro-3-hydroxy derivatives.

According to a second aspect of the present invention, there is provided a process for the preparation of compounds of the general formula (10):

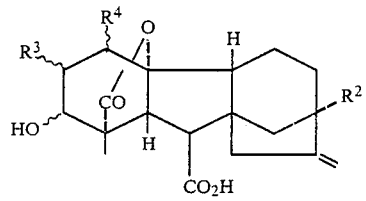
(10)

wherein the radicals $R^2$, $R^3$ and $R^4$ are as hereinbefore defined,
comprising the reaction of a 3-keto gibberellin of the general formula (13):

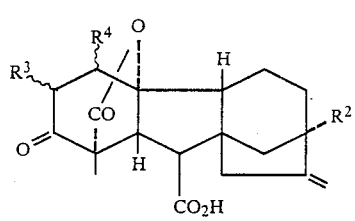
(13)

wherein the radicals $R^2$, $R^3$ and $R^4$ are as hereinbefore defined,
with a compound of the general formula (12):

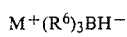
$M^+(R^6)_3BH^-$ (12)

wherein $M^+$ represents a monovalent cation and $R^6$ represents an alkyl group.

Although, in this second aspect of the present invention, it is not essential to have an in situ proton source to decompose any initial borate complex, it has been found advantageous to include such a source to buffer the reaction mixture. Several proton sources can be used, including alkanols and hydrogenphosphate salts. Preferably, the proton source is selected from ethanol, isopropanol, potassium or sodium dihydrogenphosphate, or dipotassium hydrogenphosphate. More preferably, potassium dihydrogenphosphate is used, as this proton source buffers the reaction mixture without rapidly destroying the trialkylborohydrides.

The discovery that the presence of this additional proton source does not adversely affect the above process allows the conversion of a mixture of $\Delta(1)$-3-keto- and 1,2-dihydro-3-keto gibberellins directly into the corresponding 1,2-dihydro-3-hydroxy gibberellins, without having to first separate the initial mixture into its individual components.

Thus, according to a third aspect of the present invention, there is provided a process for the preparation of compounds of the general formula (10):

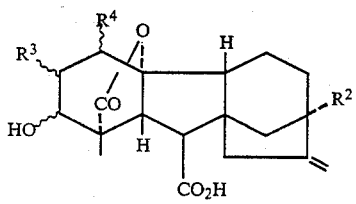

wherein the radicals $R^2$, $R^3$ and $R^4$ are as hereinbefore defined, comprising the reaction of a mixture of 3-keto gibberellins of the general formulae (11) and (13):

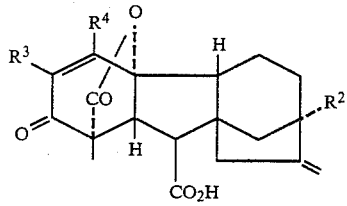  (11)

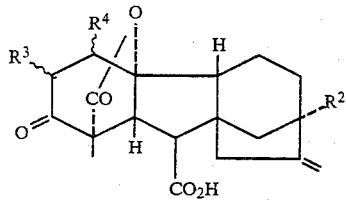  (13)

wherein the radicals $R^2$, $R^3$ and $R^4$ are as hereinbefore defined, in the presence of a proton source, with a compound of the general formula (12):

$$M^+(R^6)_3BH^- \qquad (12)$$

wherein $M^+$ represents a monovalent cation and $R^6$ represents an alkyl group.

As used throughout the specification, the cation $M^+$ represents any suitable monovalent cation, including sodium, lithium, potassium and tetra-alkylammonium ions.

For all the processes of the present invention, the trialkylborohydrides of general formula (12) are preferably the lithium and potassium tri-sec-butylborohydrides or potassium triethylborohydride.

In particular, potassium tri-sec-butylborohydride is preferred if the naturally occurring 3β-hydroxy gibberellins are required, while both lithium tri-sec-butylborohydride and potassium triethylborohydride are preferred for the preparation of the 3α-epimers.

Compounds of general formulae (11) and (13) are either known, or can be prepared from known compounds by standard reactions well known in the art. For example, GA$_7$(4) is a naturally occurring compound and oxidation with chromium trioxide, as described for the oxidation of the C(7)methylester by L Lombardo, L N Mander and J V Turner, *Aust. J. Chem.*, 34, 745 (1981) produces the ketone (14a). Similarly, by following an analogous procedure, oxidation of GA$_4$(3) with chromium trioxide affords the ketone (14b), and oxidation of a mixture of GA$_4$(3) and GA$_7$(4) affords a mixture of the ketones (14a) and (14b).

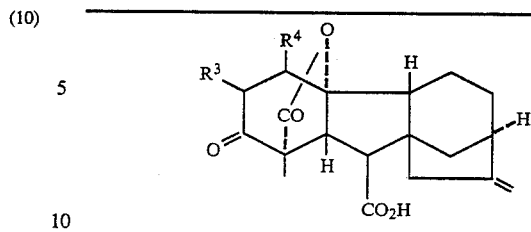

| | | |
|---|---|---|
| (14a) | together, a valence bond | |
| (14b) | H | H |

Similarly, GA$_3$(2) is a known compound and oxidation with manganese dioxide [P J Keay, J S Moffatt and T P C Mulholland, *J. Chem. Soc.*, 1605 (1965)] or pyridinium dichromate [following a procedure analogous to that described for the corresponding methyl ester by Z J Duri, B M Fraga and J R Hanson, *J.C.S. Perkin*, 1, 161 (1981)] produces the ketone (15):

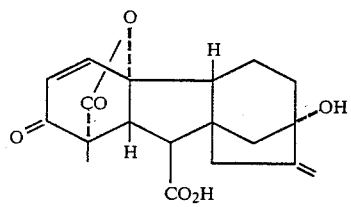  (15)

The trialkylborohydrides of general formula (12) are readily prepared by known procedures [see, for example, J M Fortunato and B Ganem, *J. Org. Chem.*, 41, 2194 (1976)].

The reaction conditions required for the hydride reduction processes of the present invention are usually carried out at low temperatures and under an inert atmosphere. Generally, it has been found that a temperature range of about −80 degrees C. to about −5 degrees C. has been satisfactory. In particular, for the preparation of compounds of general formula (10), using the hydrogenphosphate salts as the proton source, a temperature range of about −70 degrees C. to about −10 degrees C. has resulted in good yields of the required products. If alkanols are the proton source, a temperature range of about −35 degrees C. to about −25 degrees C. is preferred.

Preferably, the radicals $R^3$ and $R^4$ are separately selected from the group consisting of hydrogen, methyl and ethyl, and $R^2$ is a radical selected from the group consisting of H, OH, methoxy, methoxymethoxy, acetoxy and dichloroacetoxy. Most preferably, $R^3$ and $R^4$ both represent H and $R^2$ represents OH, or the radicals $R^2$, $R^3$ and $R^4$ all represent H.

Thus the reaction of the ketone (14a):

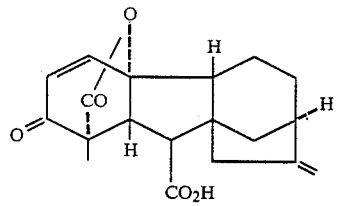  (14a)

in the presence of a proton source, with potassium tri-sec-butylborohydride, affords the naturally occurring gibberellin GA$_4$(3):

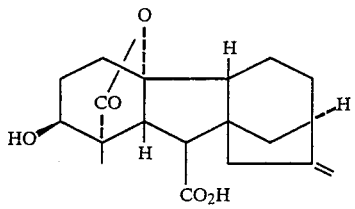

(3)

Similarly, the reaction of the ketone (14b):

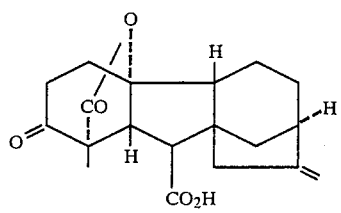

(14b)

with potassium tri-sec-butylborohydride, also affords the naturally occurring gibberellin GA$_4$(3).

The gibberellin GA$_4$(3) is also produced from the reaction of a mixture of the ketones (14a) and (14b), in the presence of a proton source, with potassium tri-sec-butylborohydride.

By similar processes to those described above in respect of the ketone (14a):

(a) the reaction of the ketone (15), in the presence of a proton source; or
(b) the reaction of the ketone (18); or
(c) the reaction of a mixture of the ketones (15) and (18), in the presence of a proton source;

with potassium tri-sec-butylborohydride produces the naturally occurring gibberellin GA$_1$(19).

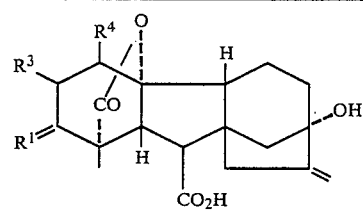

| | R$^1$ | R$^3$ | R$^4$ |
|---|---|---|---|
| (15) | O | together, a valence bond | |
| (18) | O | H | H |
| (19) | βOH, αH | H | H |

If potassium tri-sec-butylborohydride is replaced with lithium tri-sec-butylborohydride or potassium triethylborohydride, in the above preferred reaction procedures, then the epimeric 3α-hydroxy gibberellins of the general formula (20):

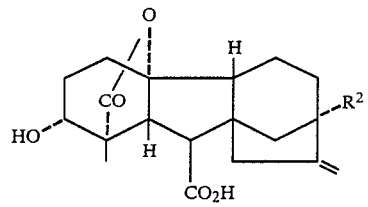

(20)

wherein the radical R$^2$ represents H or OH, are the products.

The processes described above could also be carried out on other gibberellins—for example, on C20-gibberellins, and their analogues, as represented by the compounds of the general formula (21):

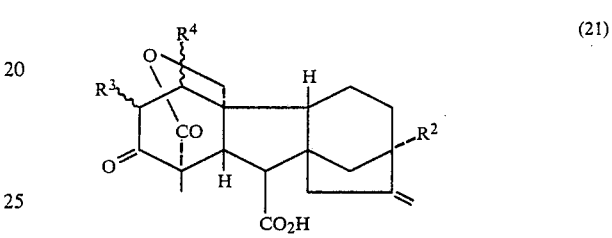

(21)

wherein

R$^2$ is a radical selected from the group consisting of H, OH, alkoxy, substituted alkoxy and acyloxy;

R$^3$ and R$^4$ are radicals separately selected from the group consisting of H and alkyl; or together, represent a valence bond.

Specific details of the compounds of the present invention and the reactions involved in the processes of this invention are illustrated by the following examples. In these examples, all temperatures are in degrees centigrade, and technical terms (e.g. chromatography, etc.) have the usual meaning in the art. Crude reaction products can be purified by the means described herein, or by other means known in the art.

EXAMPLE A isolation of GA$_4$(3) and GA$_7$(4) from a commercially available GA$_4$/GA$_7$ mixture A technical mixture of GA$_4$(3) and GA$_7$(4) was subjected to reverse-phase HPLC (Waters, μBondpak C18) using methanol-water (55:45) as eluant at a flow rate of 4 ml/min. GA$_7$(4) was eluted first (15 min) followed by GA$_4$(3) (17 min).

EXAMPLE B (a) oxidation of GA$_4$(3) to the corresponding 3-keto gibberellin (14b)

GA$_4$(3) (8 g) was dissolved in acetone (600 ml) and cooled to about 0 degrees. Jones' reagent (about 10 ml) was added dropwise to the stirred solution up to an orange end-point and when the oxidation was complete (TLC) sufficient propan-2-ol was added to destroy the excess of oxidant. The reaction mixture was concentrated under reduced pressure, and the residue partitioned between dichloromethane and brine (50% sat.). After drying (Na$_2$SO$_4$), the dichloromethane was evaporated to afford the 3-keto gibberellin (14b) which had consistent $^1$H-nmr data and physical characteristics as reported by C D Aldridge, J R Hanson and T P C Mulholland, *J. Chem. Soc.*, 3539 (1965).

(b) oxidation of GA$_7$(4) to the corresponding 3-keto gibberellin (14a)

In a reaction analogous to the oxidation of GA$_4$(3) to the ketone (14b) described above, GA$_7$(4) was dissolved in acetone, cooled, and Jones' reagent added until the oxidation was complete. The 3-keto gibberellin (14a) was isolated from the crude reaction mixture in a similar procedure to that described above for the isolation of the ketone (14b).

(c) oxidation of a mixture of GA$_4$(3) and GA$_7$(4) to the corresponding mixture of ketones (14b) and (14a) respectively In a reaction analogous to the oxidation of GA$_4$(3) to the ketone (14b) described above, a mixture of GA$_4$(3) and GA$_7$(4) was dissolved in acetone, cooled, and Jones' reagent added until the oxidation was complete. A mixture of the ketones (14a) and (14b) was isolated from the crude reaction mixture in a similar procedure to that described above for the isolation of the pure ketone (14b).

EXAMPLE C oxidation of GA$_3$(2) to the corresponding 3-keto gibberellin (15)

Pyridinium dichromate (6.5 mmol) was added to a stirred solution of GA$_3$(2) (2.9 mmol) in dimethylformamide (6 ml) at about 0 degrees. After about 3 hrs at 20 degrees, the reaction mixture was partitioned between dichloromethane and brine (50% containing 2% phosphoric acid) and the concentrated organic layer chromatographed on silica (activity 3, eluant: ether/dichloromethane/acetic acid/methanol, 20/20/1/1) to afford the 3-keto gibberellin (15). The ketone (15) had consistent $^1$H-nmr data and physical characteristics as reported by P J Keay, J S Moffatt and T P C Mulholland, *J. Chem. Soc.*, 1605 (1965).

EXAMPLE 1 reduction of 3-keto gibberellin acid (14a) to GA$_4$(3)

Potassium tri-sec-butylborohydride (16 mmol) in tetrahydrofuran (THF) was added over about 15 min to a stirred solution under nitrogen of 3-keto gibberellin acid (14a) (4 mmol) in THF (40 ml) at −70 degrees (internal thermometer) containing dry, powdered potassium dihydrogenphosphonate (24 mmol). The mixture was brought to −30 degrees during 30 min, then slowly to 0 degrees. As soon as TLC (quench −70 degrees) indicated that no ketone remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: light petrol/ether/dichloromethane/acetic acid/methanol, 42/20/20/1/1) to give GA$_4$(3) which had consistent $^1$H-nmr data, and physical characteristics as reported by B E Cross, R H B Galt and J R Hanson, *Tetrahedron*, 18, 451 (1962).

EXAMPLE 2 reduction of 3-keto gibberellin acid (14a) to GA$_4$(3)

Potassium tri-sec-butylborohydride (16 mmol) in THF was added over about 15 min to a stirred solution under nitrogen of 3-keto gibberellin acid (14a) (4 mmol) in THF (40 ml) at −30 degrees (internal thermometer) containing dry ethanol (24 mmol). The mixture was brought slowly to 0 degrees. As soon as TLC (quench −30 degrees) indicated that no ketone remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: light petrol/ether/dichloromethane/acetic acid/methanol, 42/20/20/1/1) to give GA$_4$(3) which had physical characteristics as reported in the literature and consistent $^1$H-nmr data.

EXAMPLE 3 reduction of 3-keto gibberellin acid (14b) to GA$_4$(3)

Potassium tri-sec-butylborohydride (16 mmol) in THF was added over about 15 min to a stirred solution under nitrogen of 3-keto gibberellin acid (14b) (4 mmol) in THF (40 ml) at −70 degrees (internal thermometer). The mixture was brought to −30 degrees during 30 min, then slowly to 0 degrees. As soon as TLC (quench −70 degrees) indicated that no ketone remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: light petrol/ether/dichloromethane/acetic acid/methanol, 42/20/20/1/1) to give GA$_4$(3) which had physical characteristics as reported in the literature and consistent $^1$H-nmr data.

EXAMPLE 4 reduction of a mixture of the 3-keto gibberellin acids (14a) and (14b) to GA$_4$(3)

Potassium tri-sec-butylborohydride (16 mmol) in THF was added over about 15 min to a stirred solution under nitrogen of a mixture of the 3-keto gibberellin acids (14a) and (14b) (4 mmol) in THF (40 ml) at −70 degrees (internal thermometer) containing dry, powdered potassium dihydrogenphosphate (24 mmol). The mixture was brought to −30 degrees during 30 min, then slowly to 0 degrees. As soon as TLC (quench −70 degrees) indicated that no ketones remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: light petrol/ether/dichloromethane/acetic acid/methanol, 42/20/20/1/1) to give GA$_4$(3) which had physical characteristics as reported in the literature and consistent $^1$H-nmr data.

EXAMPLE 5 reduction of a mixture of the 3-keto gibberellin acids (14a) and (14b) to 3α-hydroxy gibberellin (20a)

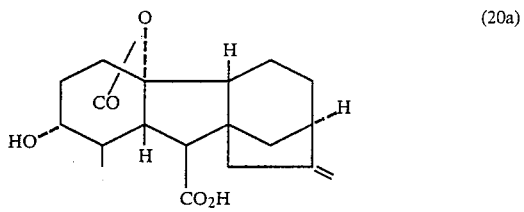
(20a)

Potassium triethylborohydride (16 mmol) in THF was added over about 15 min to a stirred solution under nitrogen of a mixture of the 3-keto gibberellin acids (14a) and (14b) (4 mmol) in THF (40 ml) at −70 degrees (internal thermometer) containing dry, powdered potassium dihydrogenphosphate (24 mmol). The mixture was brought to −30 degrees during 30 min, then slowly to 0 degrees. As soon as TLC (quench −70 degrees) indicated that no ketones remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: light petrol/ether/dichloromethane/acetic acid/methanol, 42/20/20/1/1) to give the 3α-hydroxy gibberellin (20a).

EXAMPLE 6 reduction of 3-keto gibberellin acid (15) to GA$_1$(19)

3-Keto gibberellin acid (15) (4 mmol) was dissolved in THF containing dry, powdered potassium dihydrogenphosphate (24 mmol), at 50 degrees, and the resultant solution cooled to −70 degrees. Potassium tri-sec-butylborohydride (16 mmol) was added over about 15 min to the above solution under a nitrogen atmosphere. The mixture was brought slowly to 0 degrees. As soon as TLC (quench −70 degrees) indicated that no ketone remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica (activity 3, eluant: ether/dichloromethane/acetic acid/methanol, 20/20/1/1) to give GA$_1$(19) which had the physical characteristics as reported by J MacMillan, J C Seaton and P J Suter, *Tetrahedron*, 11, 60 (1960) and L Lombardo, L N Mander and J V Turner, *J. Amer. Chem. Soc.*, 102, 6626 (1980).

EXAMPLE 7 reduction of 3-keto-13-acetoxy gibberellin acid (22a) to the 3β-hydroxy-13-acetoxy gibberellin acid (22b)

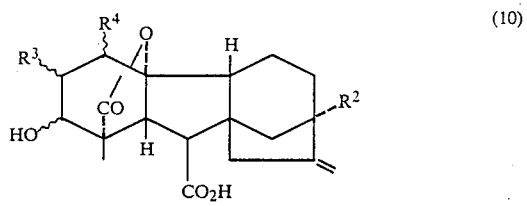

|       | $R^1$    | $R^3$ | $R^4$ |
|-------|----------|-------|-------|
| (22a) | O        | together, a valence bond | |
| (22b) | βOH, αH  | H     | H     |

Potassium tri-sec-butylborohydride (16 mmol) in tetrahydrofuran THF was added over about 15 min to a stirred solution under nitrogen of 3-keto gibberellin acid (22a) (4 mmol) in THF (40 ml) at −70 degrees (internal thermometer) containing dry, powdered potassium dihydrogenphosphate (24 mmol). The mixture was brought to −30 degrees during 30 min, then slowly to 0 degrees. As soon as TLC (quench −70 degrees) indicated that no ketone remained, the cooled (to less than −10 degrees) mixture was quenched with an ice-cold solution of potassium dihydrogenphosphate (20%, 4 ml) and the pH adjusted to about 3 with phosphoric acid (10%). The mixture was concentrated under reduced pressure to about 15 ml then diluted with dichloromethane (100 ml) and washed with brine (50% sat.). The concentrated solution was chromatographed on silica to give the 3β-hydroxy-13-acetoxy gibberellin acid (22b).

We claim:

1. A process for the preparation of compounds of the formula (10):

(10)

wherein $R^2$ is a radical selected from the group consisting of H; OH; unsubstituted alkoxy, alkoxy substituted by one or more radicals separately selected from the group consisting of alkyl, alkenyl, alkynyl, alkoxy and halogen; and acyloxy, wherein acyloxy is a radical derived from carboxylic or sulphonic acids, which is unsubstituted or substituted by one or more radicals separately selected from the group consisting of alkyl, alkenyl, alkynyl, alkoxy and halogen;

$R^3$ and $R^4$ are radicals separately selected from the group consisting of H and alkyl;

characterised in that the process comprises the reaction of a Δ(1)-3-keto gibberellin of the formula (11):

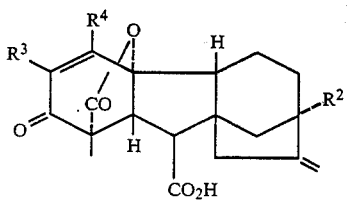
(11)

wherein $R^2$, $R^3$ and $R^4$ are as defined above; with a compound of the formula (12):

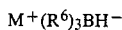 (12)

wherein $M^+$ represents a monovalent cation and $R^6$ represents an alkyl group; and the reaction is conducted in the presence of a proton source which will decompose in situ the initial intermediate enol borate formed between the compounds of formulae (11) and (12) without affecting the structural integrity of the carbon skeleton of the compounds of the formula (10).

2. A process for the preparation of compounds of the formula (10):

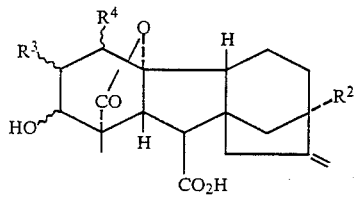 (10)

characterised in that the process comprises the reaction of a 3-keto gibberellin of the formula (13):

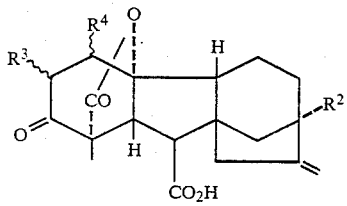 (13)

with a compound of the formula (12):

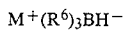 (12)

wherein $M^+$ represents a monovalent cation and the radicals $R^2$, $R^3$, $R^4$ and $R^6$ are as defined in claim 1.

3. A process for the preparation of compounds of the formula (10):

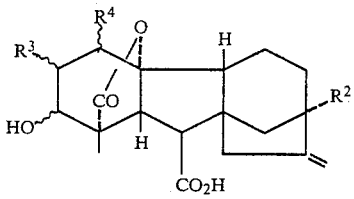 (10)

characterised in that the process comprises the reaction of a mixture of 3-keto gibberellins of the formulae (11) and (13):

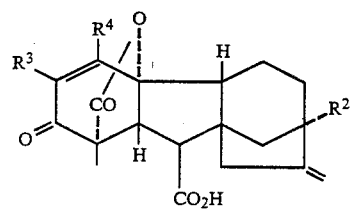 (11)

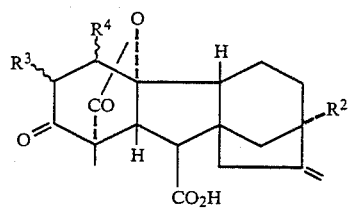 (13)

with a compound of the formula (12):

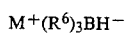 (12)

wherein $M^+$ represents a monovalent cation and the radicals $R^2$, $R^3$, $R^4$ and $R^6$ are as defined in claim 1; and the reaction is conducted in the presence of a proton source which will decompose in situ the initial intermediate enol borate formed between the compounds of formulae (11) and (12) without affecting the structural integrity of the carbon skeleton of the compounds of the formula (10).

4. A process as defined in claim 1 or claim 3, wherein the proton source is selected from an alkanol or a hydrogenphosphate salt.

5. A process as defined in claim 1 or claim 3, wherein the proton source is selected from potassium dihydrogenphosphate, sodium dihydrogenphosphate and dipotassium hydrogenphosphate.

6. A process as defined in claim 1 or claim 2 or claim 3, wherein the compound of formula (12) represents lithium tri-sec-butylborohydride, potassium tri-sec-butylborohydride or potassium triethylborohydride.

7. A process as defined in claim 1 or claim 3, wherein the proton source is selected from potassium dihydroghenphosphate, sodium dihydrogenphosphate, and dipotassium hydrogenphosphate and the compound of formula (12) represents lithium tri-sec-butylborohydride, potassium tri-sec-butylborohydride or potassium triethylborohydride.

8. A process as defined in claim 1 or claim 2 or claim 3, wherein the radicals $R^3$ and $R^4$ are separately selected from the group consisting of H, methyl and ethyl; and wherein $R^2$ is a radical selected from the group consisting of H, OH, methoxy, methoxymethoxy, acetoxy and dichloroacetoxy.

9. A process as defined in claim 1 or claim 3, wherein the radicals $R^3$ and $R^4$ are separately selected from the group consisting of H, methyl and ethyl; $R^2$ is a radical selected from the group consisting of H, OH, methoxy, methoxymethoxy, acetoxy and dichloroacetoxy; the proton source is selected from potassium dihydrogenphosphate, sodium dihydrogenphosphate and dipotassium hydrogenphosphate; and the compound of formula (12) represents lithium tri-sec-butylborohydride, potassium tri-sec-butylborohydride or potassium triethylborohydride.

10. A process as defined in claim 2, wherein the radicals $R^3$ and $R^4$ are separately selected from the group consisting of H, methyl and ethyl; $R^2$ is a radical selected from the group consisting of H, OH, methoxy, methoxymethoxy, acetoxy and dichloroacetoxy; and the compound of formula (12) represents lithium tri-sec-butylborohydride, potassium tri-sec-butylborohydride or potassium triethylborohydride.

11. A process as defined in claim 1 or claim 2 or claim 3, wherein the radicals $R^2$, $R^3$ and $R^4$ all represent H.

12. A process as defined in claim 2, wherein the radicals $R^2$, $R^3$ and $R^4$ all represent H and the compound of formula (12) represents lithium tri-sec-butylborohydride, potassium tri-sec-butylborohydride or potassium triethylborohydride.

13. A process as defined in claim 1 or claim 3, wherein the radicals $R^2$, $R^3$ and $R^4$ all represent H; the compound of formula (12) represents lithium tri-sec-butylborohydride, potassium tri-sec-butylborohydride or potassium triethylborohydride; and the proton source is selected from potassium dihydrogenphosphate, sodium dihydrogenphosphate and dipotassium hydrogenphosphate.

14. A process as defined in claim 1 or claim 2 or claim 3, wherein the radicals $R^3$ and $R^4$ both represent H and the radical $R^2$ represents OH.

15. A process as defined in claim 2, wherein the radicals $R^3$ and $R^4$ both represent H; the radical $R^2$ represents OH; and the compound of formula (12) represents lithium tri-sec-butylborohydride, potassium tri-sec-butylborohydride or potassium triethylborohydride.

16. A process as defined in claim 1 or claim 3, wherein the radicals $R^3$ and $R^4$ both represent H; the radical $R^2$ represents OH; the compound of formula (12) represents lithium tri-sec-butylborohydride, potassium tri-sec-butylborohydride or potassium triethylborohydride; and the proton source is selected from potassium dihydrogenphosphate, sodium dihydrogenphosphate and dipotassium hydrogenphosphate.

17. A process for the preparation of compounds of the formula (10a):

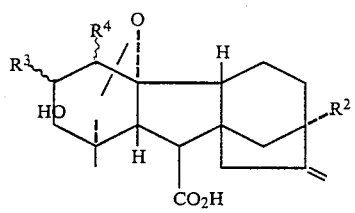
(10a)

characterised in that the process comprises the reaction of a Δ(1)-3-keto gibberellin of the formula (11):

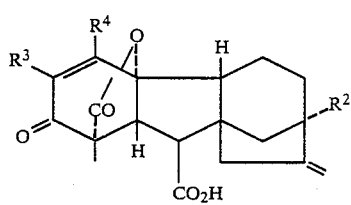
(11)

with potassium tri-sec-butylborohydride, wherein the radicals $R^2$, $R^3$ and $R^4$ are as defined in claim 1; and the reaction is conducted in the presence of a proton source which will decompose in situ the initial intermediate enol borate formed between the compounds of formulae (11) and (12) without affecting the structural integrity of the carbon skeleton of the compounds of the formula (10).

18. A process for the preparation of compounds of the formula (10a):

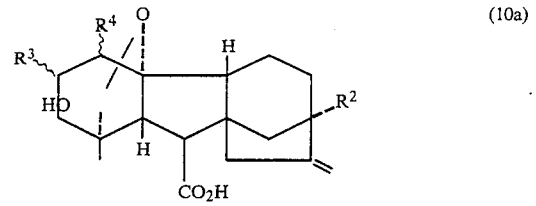
(10a)

characterised in that the process comprises the reaction of a 3-keto gibberellin of the formula (13):

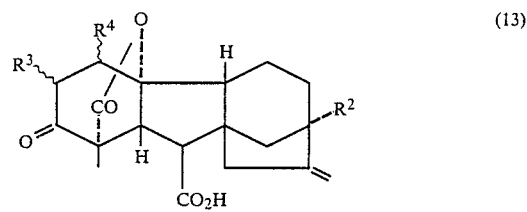
(13)

with potassium tri-sec-butylborohydride, wherein the radicals $R^2$, $R^3$ and $R^4$ are as defined in claim 1.

19. A process for the preparation of compounds of the formula (10a):

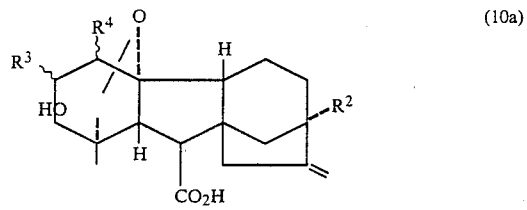
(10a)

characterised in that the process comprises the reaction of a mixture of 3-keto gibberellins of the formulae (11) and (13):

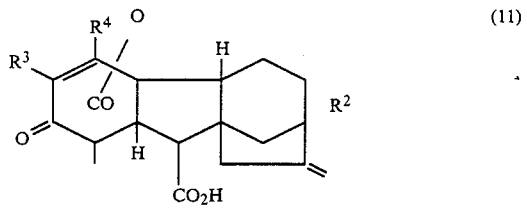
(11)

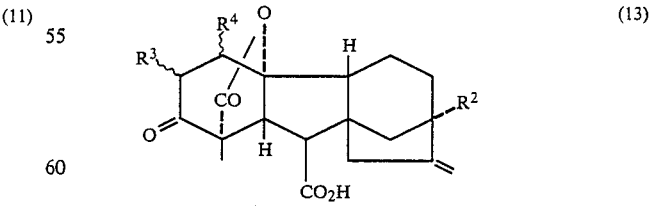
(13)

wherein the radicals $R^2$, $R^3$ and $R^4$ are as defined in claim 1, with potassium tri-sec-butylborohydride; and the reaction is conducted in the presence of a proton source which will decompose in situ the initial intermediate enol borate formed between the compounds of formulae (11) and (12) without affecting the structural integrity of the carbon skeleton of the compounds of formula (10).

20. A process as defined in claim 17 or claim 19, wherein the proton source is selected from an alkanol or a hydrogenphosphate salt.

21. A process as defined in claim 17 or claim 19, wherein the proton source is selected from potassium dihydrogenphosphate, sodium dihydrogenphosphate and dipotassium hydrogenphosphate.

22. A process as defined in claim 17 or claim 18 or claim 19, wherein the radicals $R^3$ and $R^4$ are separately selected from the group consisting of H, methyl and ethyl; and wherein $R^2$ is a radical selected from the group consisting of H, OH, methoxy, methoxymethoxy, acetoxy and dichloroacetoxy.

23. A process as defined in claim 17 or claim 19, wherein the radicals $R^3$ and $R^4$ are separately selected from the group consisting of H, methyl and ethyl; $R^2$ is a radical selected from the group consisting of H, OH, methoxy, methoxymethoxy, acetoxy and dichloroacetoxy; and the proton source is selected from potassium dihydrogenphosphate, sodium dihydrogenphosphate and dipotassium hydrogenphosphate.

24. A process as defined in claim 17 or claim 18 or claim 19, wherein the radicals $R^2$, $R^3$ and $R^4$ all represent H.

25. A process as defined in claim 17 or claim 19, wherein the radicals $R^2$, $R^3$ and $R^4$ all represent H; and the proton source is selected from potassium dihydrogenphosphate, sodium dihydrogenphosphate and dipotassium hydrogenphosphate.

26. A process as defined in claim 17 or claim 18 or claim 19, wherein the radicals $R^3$ and $R^4$ both represent H and the radical $R^2$ represents OH.

27. A process as defined in claim 17 or claim 19, wherein the radicals $R^3$ and $R^4$ both represent H; the radical $R^2$ represents OH; and the proton source is selected from potassium dihydrogenphosphate, sodium dihydrogenphosphate and dipotassium hydrogenphosphate.

* * * * *